United States Patent
Putz

(10) Patent No.: US 7,073,729 B2
(45) Date of Patent: Jul. 11, 2006

(54) JEWELRY FOR EMITTING FRAGRANCES AND A METHOD THEREFOR

(75) Inventor: Lawrence J. Putz, Grand Junction, CO (US)

(73) Assignee: Panache Porcelain, LLC, Grand Junction, CO (US)

( * ) Notice: Subject to any disclaimer, the term of this patent is extended or adjusted under 35 U.S.C. 154(b) by 534 days.

(21) Appl. No.: 10/050,596

(22) Filed: Jan. 15, 2002

(65) Prior Publication Data

US 2002/0117556 A1    Aug. 29, 2002

Related U.S. Application Data

(63) Continuation-in-part of application No. 09/114,009, filed on Jul. 10, 1998, now Pat. No. 6,367,706.

(51) Int. Cl.
*A24J 25/00* (2006.01)
*A61L 9/04* (2006.01)
*B05B 9/00* (2006.01)

(52) U.S. Cl. ............................ 239/36; 239/53; 239/57; 239/326; 239/51.5

(58) Field of Classification Search ................ 239/34, 239/36, 44, 51.5, 53, 55, 56, 57, 326; 63/1.14, 63/1.15 X, DIG. 2
See application file for complete search history.

(56) References Cited

U.S. PATENT DOCUMENTS

| | | | | |
|---|---|---|---|---|
| 367,976 A | * | 8/1887 | Hartmann | .................... 239/55 |
| 1,683,545 A | * | 9/1928 | Harris | .......................... 63/1.15 |
| 1,780,408 A | * | 11/1930 | Smith | ........................... 239/36 |
| 3,784,102 A | * | 1/1974 | Stutts | ........................... 239/36 |
| 4,056,951 A | * | 11/1977 | Black | ............................. 63/13 |
| 4,159,631 A | * | 7/1979 | Lee | ............................. 63/1.15 |
| 4,283,011 A | * | 8/1981 | Spector | ....................... 239/36 |
| 4,306,679 A | * | 12/1981 | Dusek et al. | ................. 239/59 |
| 4,869,407 A | * | 9/1989 | Booth et al. | ................... 222/3 |
| 5,000,780 A | * | 3/1991 | Tokunaga | ..................... 75/246 |
| 5,735,460 A | * | 4/1998 | Eisenbraun | .................. 239/34 |

FOREIGN PATENT DOCUMENTS

DE        197 53 956 A  *  12/1997

* cited by examiner

*Primary Examiner*—Davis Hwu
(74) *Attorney, Agent, or Firm*—Timothy J. Martin; Michael R. Henson; John W. Carpenter

(57) ABSTRACT

An item of jewelry is provided to receive a fragrance composition. The jewelry piece includes a securement member, a setting, and a piece of porous material. The securement member supports the setting and enables the jewelry item to be worn by the person in the manner in which it is intended. In some embodiments, the setting supports the piece of porous material relative to the securement member such that ambient air may flow between it and the securement member, maximizing the exposed surface area of the porous material. The porous material is a ceramic that contains sintered aluminum oxide and receives a liquid fragrance producing composition such as perfume or cologne. A method for applying the fragrance to the piece of porous material is also provided and includes the step of washing the porous material with a solvent suitable to diffuse the carrier liquid of the fragrance producing composition.

26 Claims, 3 Drawing Sheets

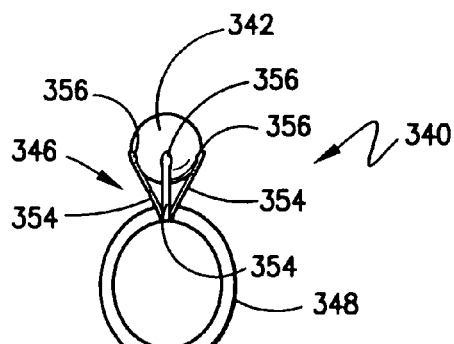
Fig.14
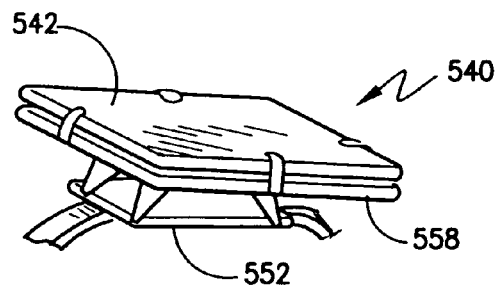
Fig.20
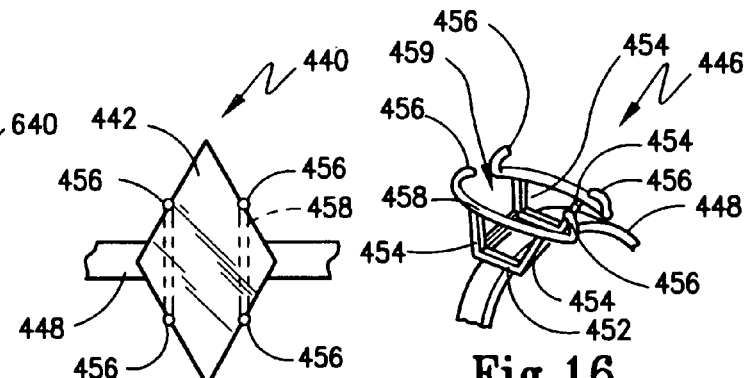
Fig.15
Fig.16
Fig.17
Fig.21
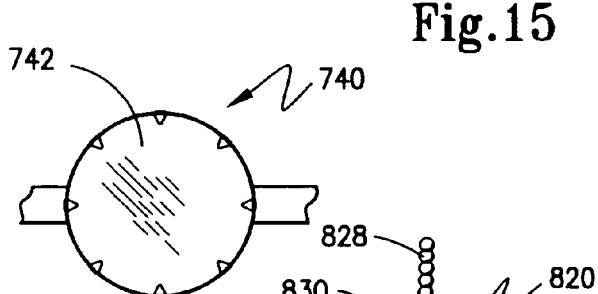
Fig.22
Fig.18
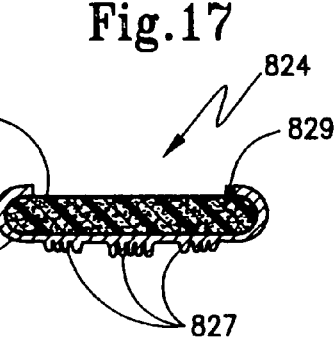
Fig.19

JEWELRY FOR EMITTING FRAGRANCES AND A METHOD THEREFOR

RELATED APPLICATION

The present application is a continuation-in-part of U.S. application Ser. No. 09/114,009 entitled "Fragrance Extending Device and Method Therefor" filed Jul. 10, 1998, now U.S. Pat. No. 6,367,706.

FIELD OF THE INVENTION

The present invention broadly concerns jewelry. More particularly, the present invention is directed to pieces of jewelry that employ porous material to receive a sufficient quantity of a selected fragrance producing composition such that the emission of the fragrance may be detected by the olfactory senses. The present invention is also directed to a method of extending the interval of time for which a fragrance may be perceived by the senses on a piece of jewelry and subsequently removing the fragrance from the jewelry so that it may be reused.

BACKGROUND OF THE INVENTION

While often less appreciated than other ones of the senses, the sense of smell has great importance both to the well-being and pleasure of existence. Various fragrances and odors are pervasive throughout the environment so that the sense of smell plays an important role in the interaction of an organism with its environment. The importance of the sense of smell exists in the detection of both pleasant and unpleasant odors.

A sense of smell can protect the organism against dangerous situations. For example, the smell of smoke can alert a human or other animal to the threat of fire. Likewise, the detection of different gases or other chemicals can serve to warn against impending danger. The detection, by the sense of smell, of tainted or spoiled food can protect the human or other animal against the ingestion of a substance that may cause sickness or death.

However, on the more pleasant side, the sense of smell enhances the enjoyment of the environment. The fragrance of flowers, plants and other organic materials can instill satisfaction and pleasure. Indeed, it has been determined that the sense of smell is actually a large component of that which is referred to as the sense of taste. Moreover, the sense of smell plays an important role in sexual attraction among animals and is essential to the reproductive cycles of many plants.

Since many people enjoy the presence of pleasant fragrances, humans have long sought to bring pleasant odors into their environment. For example, there are fiber board pads, often in a decorative shape, which are impregnated with various odors so that they may be hung in closets, automobiles and other confined spaces. These devices emit their fragrance over an interval of time after which they are typically discarded. Other devices mount into electrical outlets and use electricity to stimulate the emission of a fragrance. Another popular product is referred to as "potpourri" which is typically a mixture of dried pedals, leaves or other organic materials that are placed in an exposed container so that the fragrance of the organic materials permeates the air. Potpourri may also be encased in a cloth-like material to result in a sachet. Sachets are often placed in drawers, such as lingerie drawers, to lend a fragrance to the clothing surrounding the sachet.

In addition to devices that emit pleasant fragrances, men and women alike adorn themselves with a plethora of fragrances, both to please themselves as well as others with whom they come in contact. Many of these fragrance producing products are applied directly to the skin, and include lotions, deodorants, shaving compositions, soaps and the like.

Perhaps the most lucrative industry for fragrance producing products is the perfume industry, which is a multi-billion dollar enterprise. Unfortunately, some people are allergic to perfumes and, for various reasons, are unable to wear perfume. For example, exposure to perfume causes some women to have an allergic sinus reaction. Others, on the other hand, may be able to tolerate exposure to perfume so long as it does not directly contact their skin. Accordingly, there is a long felt need for improved ways in which individuals may adorn themselves with pleasant fragrances.

A Fragrance Extending Device and Method Therefor, was disclosed in my U.S. application Ser. No. 09/114,009, filed Jul. 10, 1998, now U.S. Pat. No. 6,367,706. In that application, the fragrance extending device broadly included a piece of porous material having sufficient porosity to permit penetration thereof by the carrier liquid and a support structure to support the porous material relative to a support surface.

The present application particularly introduces a new and unique way for individuals to wear selected fragrances without having to directly apply the fragrance to the individual's skin. The subject of the present application was derived from my previously filed parent application. In essence, I manipulated the support structure of that application so that it would take the form of a piece of jewelry. Thus, the present invention is directed, again, to the long felt need for devices and methods of employing personalized fragrances over an extended period of time.

SUMMARY OF THE INVENTION

It is an object of the present invention to provide new and useful pieces of jewelry that are both fashionable and adapted to receive a selected fragrance producing composition such that a perceptible amount of fragrance may emanate therefrom.

It is another object of the present invention to provide a method for extending the interval of time for which a fragrance may be perceived by the senses on a piece of jewelry.

It is a further object of the present invention to provide an item of jewelry that permits an individual to wear a selected fragrance without contacting the fragrance producing composition with the individual's skin or clothing.

Still a further object of the present invention is to provide a piece of jewelry that is adapted to receive a fragrance producing composition and that may be easily cleaned of the fragrance.

According to the present invention, then, a piece of jewelry is adapted to receive a quantity of a fragrance producing composition that includes a fragrance emitting substance in a carrier liquid. Here, the fragrance producing composition includes a fragrance emitting substance in a carrier liquid. Broadly, the piece of jewelry includes a securement member, a setting, and a piece of porous material.

The securement member is that portion of the piece of jewelry that is adapted to releasably secure the piece of jewelry to either the individual's skin or clothing and it also serves to support the jewelry setting. The securement member may take on a variety of forms. For example, it may be selected from a group consisting of chains, bands, hoops, earring posts, ear wires, ear clips, pins, hair clasps, etc. Thus, the present invention contemplates a wide variety of jewelry, including necklaces, rings, earrings, bracelets, barrettes, and brooches.

The setting supports the piece of porous material at an orientation relative to the securement member such that ambient air can flow between the piece of porous material and the securement member. Similar to the securement member, the setting may also be configured in a variety of forms. For example, the setting could be a bezel configured as a clamp that secures about the piece of porous material. Alternatively, the setting may simply include a plurality of stanchions extending from the securement member to support the piece of porous material in spaced relation to the securement member. The stanchions that extend from securement member may include extensions called prongs that form the upper end portion of the stanchions and curve inwardly toward one another to retain the piece of porous material in the setting. Yet another alternative setting could be a more complex structure, including both a base and a collet in addition to the stanchions and prongs. In this form, the stanchions may be secured to the base to support the collet in spaced relation to the base. The collet, then, supports the piece of porous material in spaced relation to the base. A plurality of prongs may be associated with the collet to retain the piece of porous material thereon wherein at least some of these prongs may be formed as extensions of the stanchions.

In this form, the collet may be formed as a piece of material that extends about an axis to define an open interior region such that when the piece of porous material is supported by the collet, a portion of its bottom surface is exposed to the ambient air. Both the base and collet may have a shape selected from a group consisting of circles, ovals, and n-sided polygons where n is an integer that is greater than two. Further, there may exist a decorative lattice that extends between the base and the collet.

The third component of the piece of jewelry contemplated by the present invention, as mentioned above, is the piece of porous material. The piece of porous material is a ceramic material, such as sintered aluminum oxide or a composition containing sintered aluminum oxide. The sintered aluminum oxide preferably has a particle size of 4–7 micrometers, inclusively. The piece of porous material may be configured as a sphere. Alternatively, the piece of porous material may be configured as a flat piece having a shape selected from a group consisting of circles, ovals, and n-sided polygons where n is an integer greater than 2. When configured as a flat piece, the piece of porous material may include a top surface and a bottom surface opposite the top surface wherein both the top and bottom surfaces are operative to receive the fragrance producing composition. As mentioned above, if a flat piece of porous material is seated on a collet having an open interior region, the bottom surface of the porous material may be exposed to the ambient air. Also, if desired, the piece of porous material may be larger than the collet on which it is seated such that its perimeter margin extends beyond that of the collet. Further, if desired, the piece of porous material may include a design that protrudes from its surface both to provide a decorative design and to vary the thickness of the piece of porous material thereby increasing the exposed surface area available for receiving the fragrance producing composition. This design can be ribbed to provide vanes that increase surface area.

The method according to the present invention is that of extending the interval of time for which a fragrance may be perceived by the senses on a piece of jewelry. The method includes any steps contemplated by the foregoing forms. Specifically, however, the method includes the step of applying a quantity of a fragrance producing composition to the exposed surface area of a piece of porous material, a component of the jewelry piece. Following the application of the fragrance producing composition, the method includes the step of exposing the piece of porous material to the ambient air for a selected interval of time. Following this exposure, the scent of the fragrance may be removed from the piece of porous material by washing it with a solvent suitable for diffusing the carrier of the fragrance producing composition. Isopropyl alcohol is one such suitable solvent. One way of washing the piece of porous material is by submerging it in isopropyl alcohol for two hours. Regardless of the way in which the piece of porous material is washed, it should be dry before applying another quantity of the selected fragrance producing composition. In the method, the porous material is a ceramic material, such as sintered aluminum oxide or a composition containing sintered aluminum oxide. The sintered aluminum oxide preferably has a particle size of between 4–7 micrometers, inclusively, as noted above.

These and other objects of the present invention will become more readily appreciated and understood from a consideration of the following detailed description of the exemplary embodiments when taken together with the accompanying drawings, in which:

BRIEF DESCRIPTION OF THE DRAWINGS

FIG. 14 is a front view in elevation of an alternative ring according to the present invention;

FIG. 15 is a top plan view of an alternative setting with a piece of porous material mounted thereon according to the present invention wherein the setting is in phantom;

FIG. 16 is a perspective view of the alternative setting shown in FIG. 15;

FIG. 17 is a top plan view of the alternative setting shown in FIGS. 15 and 16 without the piece of porous material mounted thereon;

FIG. 18 is a perspective view of an alternative necklace and setting;

FIG. 19 is a cross-sectional view taken about lines 19—19 of FIG. 18;

FIG. 20 is a perspective view of an alternative geometric configuration of the setting and the piece of porous material;

FIG. 21 is a top plan view of another alternative geometric configuration of the piece of porous material;

FIG. 22 is a top plan view of still another alternative geometric configuration of the piece of porous material.

DETAILED DESCRIPTION OF THE EXEMPLARY EMBODIMENTS

The present invention is directed to pieces of jewelry that are adapted to receive a quantity of a fragrance producing composition that includes a fragrance emitting substance in a carrier liquid, especially a perfume or a cologne. One purpose of this jewelry is to provide an individual with a fashionable piece of jewelry to adorn his or her body or clothing that also emanates a perceptible fragrance over a prolonged interval of time. The invention is also directed to the method of extending the interval of time for which a fragrance may be perceived by the senses on a piece of jewelry, and subsequently removing the fragrance from the jewelry so that it may be reused.

Broadly, the present invention includes a securement member, a setting supported by the securement member, and a piece of porous material supported by the setting. Each of these three components of the present invention may have a variety of different forms as will be further described below. However, in general terms, the securement member is that portion that enables the piece of jewelry to be worn in the manner in which the jewelry item is intended to be worn. Accordingly, the form of the securement member is dependent upon the type of jewelry contemplated. The setting, in general, supports the piece of porous material at an orientation relative to the securement member such that ambient air may circulate about the porous material and allow the fragrance to emanate therefrom. Finally, the piece of porous material is a material having sufficient porosity to permit penetration thereof by a carrier liquid that contains the fragrance emitting substance. The piece of porous material is a ceramic material, such as sintered aluminum oxide or a composition containing sintered aluminum oxide. It is desired that the piece of porous material have a sufficient size and exposed surface area for receiving a quantity of the fragrance producing composition adequate for the fragrance to be perceived by the olfactory senses when the piece of jewelry is worn.

Figures 1, 2, 3:
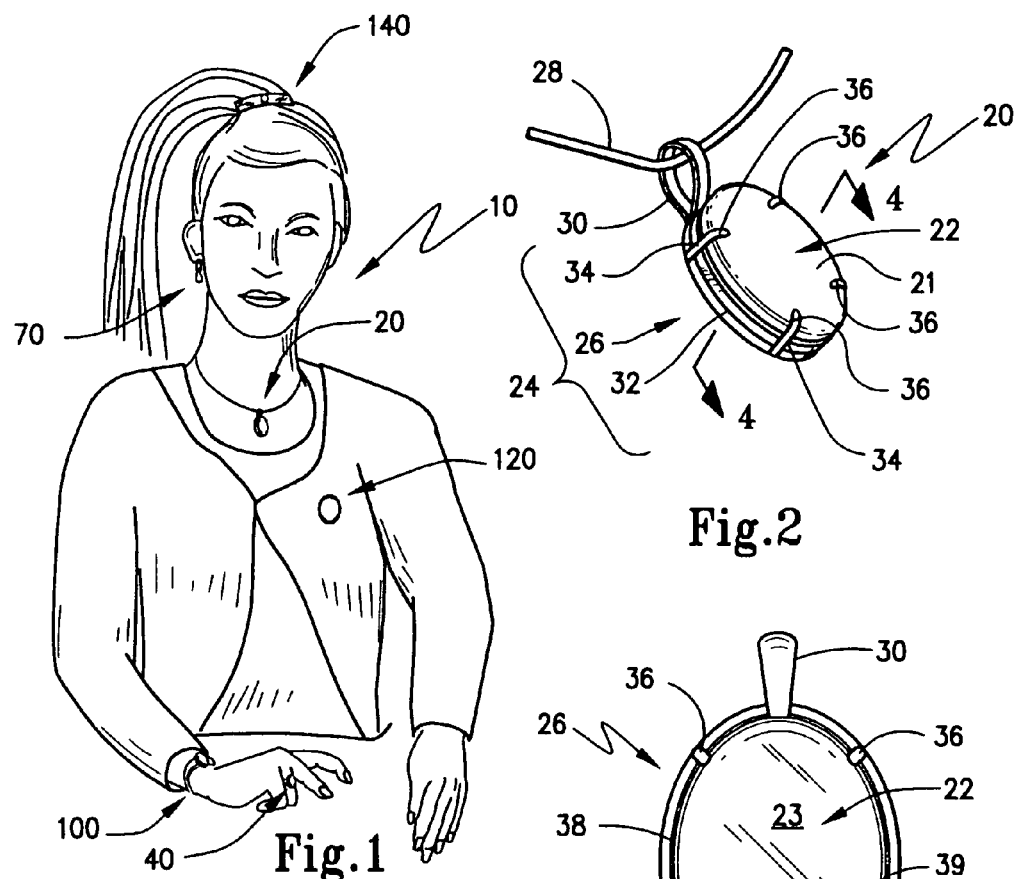
FIG. 1 is a perspective view of a woman wearing six exemplary pieces of jewelry according to the present invention.
FIG. 2 is a perspective view showing a first exemplary embodiment of the present invention, in the form of a necklace and pendant.
FIG. 3 is a back view in elevation of the pendant.

In FIG. 1, woman 10 is wearing six exemplary pieces of jewelry. As shown, woman 10 is wearing a necklace 20, a ring 40, an earring 70, a bracelet 100, a brooch 120, and a barrette 140. These six pieces of jewelry are discussed in further detail below and correspond to FIGS. 2–11.

Figures 4, 5, 6:
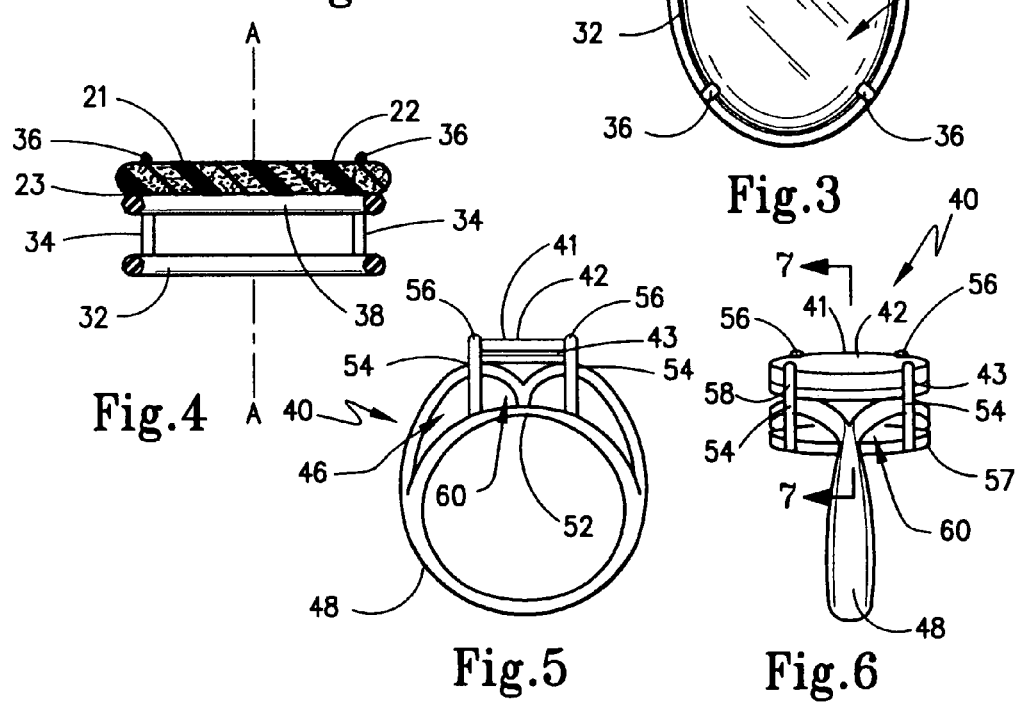
FIG. 4 is a cross-sectional view of FIG. 2 taken about lines 4—4 of FIG. 2.
FIG. 5 is a second exemplary embodiment of the present invention, in the form of a ring.
FIG. 6 is a side view in elevation of the ring of FIG. 5.

With reference to FIGS. 2–4, it may be seen that necklace 20 includes pendant 24 and chain 28. Pendant 24 is comprised of a piece of porous material 22 supported by setting 26, and loop 30 which connects pendant 24 to chain 28. Loop 30 as used here and in subsequent exemplary embodiments is sometimes also referred to in the art as an eye or hook. In this embodiment, then, the securement member is chain 28 because it is that portion of necklace 20 that enables necklace 20 to be worn about the individual's neck, and it also supports setting 26. Alternatively, setting 26 could be directly mounted to chain 28 so as to eliminate the need for loop 30, as should be appreciated by the ordinarily skilled person in this art. Further, it should be understood by the ordinarily skilled artisan, that necklace 20 may be in the form of a multi-stringed necklace rather than the single string chain shown here. Yet another alternative to the necklace 20 would be the use of a plurality of settings 26 that may be either directly mounted to chain 28 or connected by a loop 30 so that several pieces of porous material may be worn on chain 28.

As shown in FIGS. 2–4, setting 26 includes base 32, stanchions 34, prongs 36, and collet 38. Stanchions 34 are configured as posts that extend from base 32 to support collet 38 in a spaced relation to base 32. In addition, in this embodiment, each stanchion 34 has an upper end portion that is curved inwardly toward one another referred to here as prongs 36. Prongs 36 retain the piece of porous material 22 on collet 38. Further, base 32 and collet 38 are of the same size and shape as the piece of porous material 22. Both base 32 and collet 38 extend continuously about axis A so as to form an open interior region 39.

The piece of porous material 22, shown in FIGS. 2–4, is a flat, oval piece having a top surface 21 and a bottom surface 23 opposite of top surface 21. Both the top and bottom surfaces 21, 23 of the piece of porous material 22 are adapted to receive a quantity of the selected fragrance producing composition. As best shown in FIG. 3, bottom surface 23 of the piece of porous material 22 is exposed to the ambient air by open interior region 39 when seated on collet 38. Thus, both top and bottom surfaces 21, 23 are exposed to the ambient air such that the fragrance placed thereon may emanate from both surfaces. This increases the surface area available for contact by the fragrance producing composition. Further, the exposure of both top and bottom surfaces 21, 23 described above enhances the ability to thoroughly wash the piece of porous material 22 if the individual desires to remove the scent of the fragrance.

Figure 7:
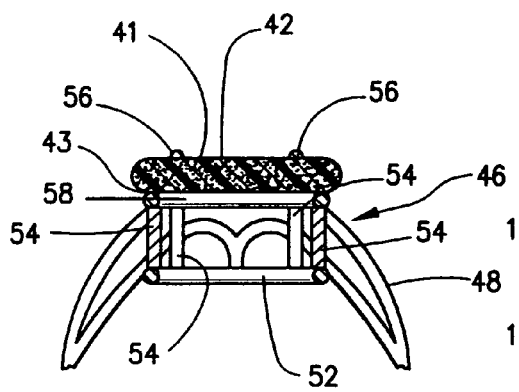
FIG. 7 is a cross-sectional view taken about lines 7—7 of FIG. 6.

A second exemplary embodiment of the present invention is ring 40. With reference to FIGS. 5–7, ring 40 is shown to include setting 46 which supports a piece of porous material 42, and band 48, which, in this instance, is the securement member. Band 48 both supports setting 46, and is that portion of ring 40 that is releasably secures it to the individual's finger. Alternatively, setting 46 could be configured to retain more than one piece of porous material as should be understood by the ordinarily skilled artisan.

Here, setting 46 includes base 52, stanchions 54, prongs 56, and collet 58. Similar to necklace 20 described above, stanchions 54 are configured as posts that extend from base 52 to support collet 58 in a spaced relation to base 52. Prongs 56 are configured as extensions of each respective stanchion 54 thereby to the upper end portion that curves inwardly toward one another to retain the piece of porous material 42 on collet 58. Further, base 52 and collet 58 are of the same size and shape of the piece of porous material 42 and form an open interior region (not shown), as did pendant 24.

The piece of porous material 42 of ring 40 is a flat, oval piece having a top surface 41 and a bottom surface 43 opposite of top surface 41. Both the top and bottom surfaces 41, 43 of the piece of porous material 42 are adapted to receive a quantity of the selected fragrance producing composition. Both surfaces 41, 43 are exposed to the ambient air so that the fragrance may emanate therefrom. In addition, FIGS. 5–7 show that ring 40 includes a decorative lattice 60 that extends between base 52 and collet 58. As shown, lattice 60 has an open framework that does not obstruct the exposure of bottom surface 43 from flow to the ambient air.

Figure 8:
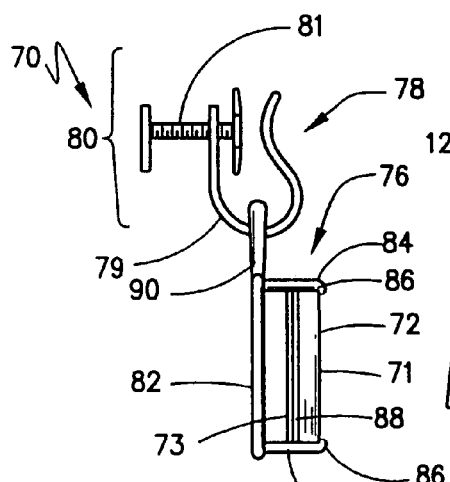
FIG. 8 is a side view in elevation of a third exemplary embodiment of the present invention, in the form of an earring.

A third exemplary embodiment of the present invention is shown in FIG. 8. Here, the piece of jewelry is in the form of a screw back earring 70. Earring 70 includes a securement member in the form of ear clip 80, setting 76 and a piece of porous material 72. Ear clip 80 releasably secures the setting to the ear lobe, and is configured as wire 79 and screw 81. Similar to necklace 20 described above, loop 90 connects setting 76 to ear clip 80. Alternatively, though, it should be appreciated that setting 76 could be directly mounted to wire 79 to eliminate the need for loop 90.

Setting 76 includes base 82, stanchions 84 that extend therefrom to support collet 88, and prongs 86. The piece of porous material 72 is a flat, oval piece having top surface 71 and bottom surface 73. As described in greater detail in the foregoing description, setting 76 is configured such that both top and bottom surfaces 71, 73 of the piece of porous material 72 are exposed to the ambient air when set therein to allow the fragrance to emanate from the piece of porous material 72.

Figure 9:
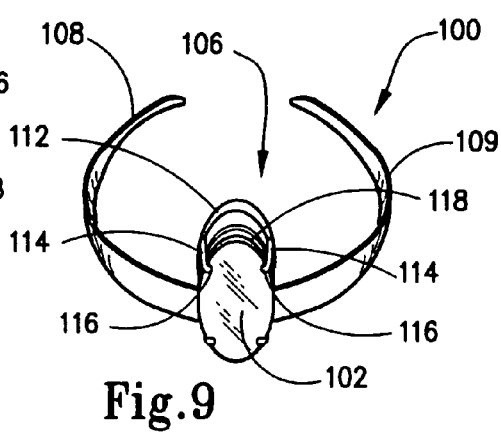
FIG. 9 is a perspective view of a fourth exemplary embodiment of the present invention, in the form of a bracelet.

A fourth exemplary embodiment of the present invention is shown in FIG. 9. Here, the piece of jewelry is a bracelet 100. Bracelet 100 includes a first band member 108, a second band member 109, setting 106, and a piece of porous material 102. First and second band members 108, 109 together form the securement member of this embodiment that may be releasably secured about an individual's wrist. Setting 106 includes base 112, stanchions 114, prongs 116 and collet 118. The ordinarily skilled artisan would understand that bracelet 100 could be releasably secured to an individual's arm by means other than band members 108, 109. For example, bracelet 100 could be secured to one's wrist by an interlocking chain.

Figures 10, 12:
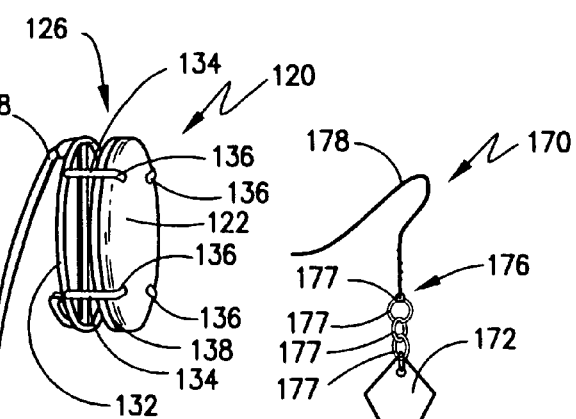
FIG. 10 is a perspective view of a fifth exemplary embodiment of the present invention, in the form of a brooch.
FIG. 12 is a perspective view of an alternative earring according to the present invention.

A fifth exemplary embodiment of the present invention is shown in FIG. 10. Here, the piece of jewelry is a brooch 120. Brooch 120 includes pin 128, setting 126, and a piece of porous material 122. Here, the securement member is in the form of pin 128. Pin 128 is adapted to releasably secure setting 126 to one's clothing. Setting 126 includes base 132, stanchions 134, prongs 136 and collet 138 described in greater detail above.

Figure 11:
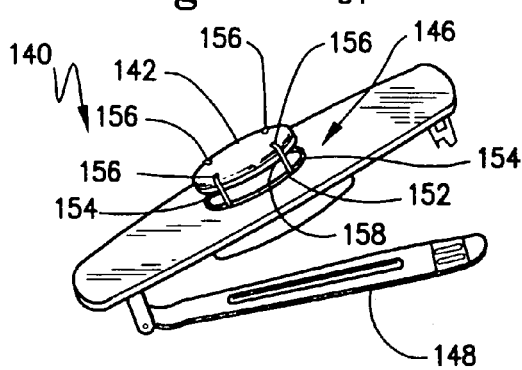
FIG. 11 is a perspective view of a sixth exemplary embodiment of the present invention, in the form of a barrette.

The sixth exemplary embodiment of the present invention is shown in FIG. 11. Here, the piece of jewelry is in the form of a barrette 140. Barrette 140 includes clasp 148, setting 146, and a piece of porous material 142. Clasp 148 is the securement member in this embodiment. Clasp 148 includes a first clasp member 147 and a second clasp member 149. Together, first and second clasp members 148, 149 releasably secure barrette 140 to an individual's hair. Setting 146 includes base 152, stanchions 154, prongs 156 and collet 158. These features have been described in greater detail with reference to FIGS. 2–4 and FIGS. 5–7 above.

The foregoing description of the six pieces of jewelry is for exemplary purposes and should not be construed as limiting this invention to only those six types of jewelry. Rather, the ordinarily skilled artisan would understand this invention to broadly incorporate all types of jewelry, including, by way of example, anklets, armlets, chokers, neck bands, belts, hair bands, combs, tie tacks, tie clasps, stick pins, and pins, to name a few. Further, it should be understood that the scope of the invention is not limited strictly to the forms of those six pieces of jewelry shown in FIGS. 1–11 described above. Rather, various alternative forms of each of the three jewelry components are contemplated. For example, in each of FIGS. 1–11, the piece of porous material is described and shown as having both a top and bottom surface that are exposed to the ambient air. Having exposure to both surfaces is desirable because it maximizes the exposed surface area for release of the fragrance. Further, the exposure of both top and bottom surfaces enhances the ability to thoroughly wash the piece of porous material should the individual desire to remove the scent of the fragrance. However, should one desire to use a large enough piece of porous material in either of the various settings, it may become unnecessary to expose the bottom surface. Accordingly, it may then be desirable to eliminate the open interior region of the collet, or it may even be possible to eliminate the collet altogether.

Figure 13:
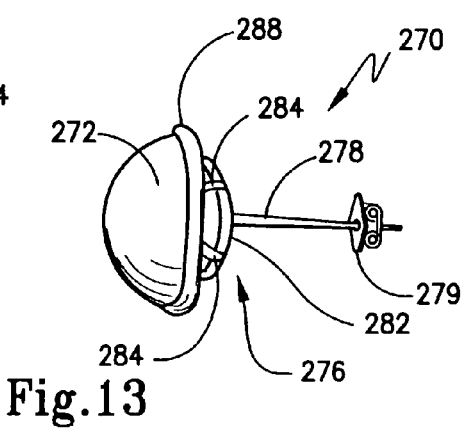
FIG. 13 is a perspective view of another alternative earring according to the present invention.

By way of illustrating some alternate examples of jewelry, FIGS. 12 and 13 provide alternative forms of earring 70 shown in FIG. 8. In FIG. 12, earring 170 is in the form of a drop earring rather than a screw back earring 70 shown in FIG. 8. Earring 170 includes an ear hook 178, setting 176, and a piece of porous material 172. Here, ear hook 178 is the securement member that secures earring 170 to an individual's ear lobe. Setting 176 is supported by ear hook 178. Setting 178 is configured as a plurality of links 177 that support the piece of porous material 172. Setting 178 includes enough links 177, to suspend the piece of porous material such that the ambient air may circulate about its entire surface area. As in the embodiments of FIGS. 1–11, the piece of porous material 172 is flat. However, unlike those described in FIGS. 1–11, this piece of porous material 172 is diamond shaped rather than oval shaped.

FIG. 13 depicts yet another possible form of earring 270. As shown therein, earring 270 includes friction post 278 and friction nut 279, which together secure earring 270 to the individual's ear lobe. Further, earring 270 includes setting 276 supported by friction post 278 and a piece of porous material 272. Here, both setting 276 and the piece of porous material 272 provide alternative forms to the earrings depicted in FIGS. 8 and 12. As shown in FIG. 13, setting 276 includes base 282, stanchions 284 extending from base 282 to support collet 288 in a spaced relation to base 282. Here, setting 276 does not include prongs. Rather, collet 288 is configured so that the piece of porous material 276 is seated within collet 288 and secured therein by means of glue, cement, or the like. Further, the piece of porous material 272 is spherical rather than a flat piece having a top and a bottom surface.

FIG. 14 shows an alternative form of ring 40 shown in corresponding FIGS. 5–7. In FIG. 14, ring 340 includes band 348, setting 346, and a piece of porous material 342. Band 348 varies merely in its decorative appearance to band 48 in FIGS. 5–7. However, the more distinguishing feature between ring 40 and ring 340 is setting 346 and the shape of the porous material 342. Setting 346 lacks both a base and a collet. Rather, stanchions 354 extend directly from band 348 to support the piece of porous material 342 such that ambient air may circulate about it. Also, each of prongs 356 are associated with a respective stanchion 354. Further, the piece of porous material 342 is configured as a spherical piece, rather than a flat piece.

Various forms of settings may also exist on each piece of jewelry contemplated by the present invention. For example, with reference to FIGS. 15–17, ring 440 includes band 448, setting 446, and a piece of porous material 442. As best seen in FIGS. 16 and 17, setting 446 includes base 452, stanchions 454 extending from base 452 to support collet 458, and prongs 456, which extend from collet 458 rather than stanchions 454. In this embodiment the both the respective shapes and sizes of base 452 and collet 458 are different. Base 452 is square shaped and smaller than collet 458 which is larger in size and in the shape of an incomplete oval. Further, the figures show that collet 485 is not strictly limited to one complete piece, but rather may be formed of two separate sections. The ordinarily skilled artisan would also understand that the collet 485 could also be configured, for example, in a horseshoe shape rather than two individual pieces. Finally, the size of the piece of porous material may vary with respect to its setting. For example, as best shown in FIG. 15, the piece of porous material 442 is larger than collet 458.

Another alternative setting is shown in FIG. 18 in the form of necklace 820. Necklace 820 includes pendant 824 and chain 828. Here, chain 28 is configured as an interlocking chain link piece. Pendant 824 is comprised of a piece of porous material 822 supported by bezel 826, and loop 830 which connects pendant 824 to chain 828. Bezel 826 is configured as an annular clamp with an interior groove 829 that encircles the piece of porous material 822 and fastens it to loop 830. Further, as best shown in FIG. 18, the piece of porous material includes a decorative design 827 on its surface. FIG. 19 shows that design 827 is ribbed such that it protrudes from the surface of the piece of porous material 822. The ribbed design 827 generates vanes so as to vary the thickness of the piece of porous material 822. This is desirable because it has the effect of increasing the available surface area of the piece of porous material 822 for receive the fragrance producing composition. The ordinarily skilled artisan would understand that the design does not have to be ribbed, but could also be flat such that it is coextensive with a flat piece of porous material. Further, the ordinarily skilled artisan would understand that the piece of porous material may exist in a variety of colors or may include a variety of decorative themes depicted thereon.

The present invention further contemplates the use of a variety of shapes of the setting and the piece of porous material which include those shapes selected from a group consisting of circles, ovals, and n-sided polygons where n is an integer that is greater than 2. For example, FIG. 18 shows a ring 540 that includes base 552, collet 558 and a piece of porous material 542 that are each shaped as diamonds. Also, base 552 is smaller in size than collet 558 and collet 558 is smaller in size than the piece of porous material 542. FIG. 19 shows ring 640 wherein the piece of porous material 642 is a hexagonal. FIG. 20 shows ring 740 wherein the piece of porous material 742 is circular in shape.

From the foregoing, it should be appreciated that the present invention is also directed to a method of extending the fragrance of a fragrance producing composition over a prolonged period of time by using a piece of jewelry. This method begins with the step of applying a quantity of a fragrance producing composition to a piece of porous material that is retained by a piece of jewelry. Following the application of the fragrance producing composition, the method includes the step of exposing the piece of porous material to the ambient air for a selected interval of time. Following this exposure, the scent of the fragrance may be removed from the piece of porous material by washing it with a solvent suitable for diffusing the carrier of the fragrance producing composition. Isopropyl alcohol is one such suitable solvent. One way in which the piece of porous material may be washed is by submerging it in isopropyl alcohol for two hours. Regardless of the way in which the piece of porous material is washed, the piece of porous material should be dry before applying another quantity of the selected fragrance producing composition.

In the method, the porous material is a ceramic material, such as sintered aluminum oxide or a composition containing sintered aluminum oxide. Preferably, the sintered aluminum oxide has a particle size of between 4–7 micrometers, inclusively, as noted above. Further, it should be understood that this method includes any step contemplated by the structure described above.

Accordingly, the present invention has been described with some degree of particularity directed to the exemplary embodiments of the present invention. It should be appreciated, though, that the present invention is defined by the following claims construed in light of the prior art so that modifications or changes may be made to the exemplary embodiments of the present invention without departing from the inventive concepts contained herein.

I claim:

1. A piece of jewelry for use by a person on said person's clothing or body, comprising:
    (a) a piece of porous material operative to receive a fragrance producing composition that includes a fragrance emitting substance in a carrier liquid;
    (b) a securement member adapted to releasably secure to a portion of the person's body or clothing; and
    (c) a setting supported by said securement member including:
        (1) a base;
        (2) a plurality of stanchions secured to said base; and
        (3) a collet supported by said stanchions in spaced relation to said base, said collet operative to support said piece of porous material in spaced relation to said base.

2. A piece of jewelry according to claim 1 including a plurality of prongs associated with said collet, said prongs having upper end portions that curve inwardly toward one another thereby to retain said piece of porous material on said collet when said piece of porous material is supported thereby.

3. A piece of jewelry according to claim 2 wherein at least some of said prongs are formed as extensions of respective ones of said stanchions.

4. A piece of jewelry according to claim 1 wherein said piece of porous material is a flat piece of material having a top surface and a bottom surface opposite said top surface and a shape selected from a group consisting of circles, ovals and n-sided polygons wherein n is an integer that is greater than 2.

5. A piece of jewelry according to claim 4 wherein said collet is formed as a piece of material that extends about an axis to define an open interior region such that when said piece of porous material is supported by said collet, a portion of said bottom surface is exposed to ambient air.

6. A piece of jewelry according to claim 1 wherein said piece of porous material is larger than said collet such that a perimeter margin of said piece of porous material extends beyond said collet.

7. A piece of jewelry according to claim 1 wherein said collet has a shape selected from a group consisting of circles, ovals, and n-sided polygons wherein n is an integer that is greater than 2.

8. A piece of jewelry according to claim 1 wherein said base member has a perimeter shape selected from a group consisting of circles, ovals, and n-sided polygons wherein n is an integer that is greater than 2.

9. A piece of jewelry according to claim 1 wherein said piece of porous material is a ceramic.

10. A piece of jewelry according to claim 9 wherein said ceramic contains sintered aluminum oxide.

11. A piece of jewelry according to claim 10 wherein said aluminum oxide has a particle size of between 4–7 micrometers, inclusively.

12. A piece of jewelry according to claim 1 wherein said securement member is selected from a group consisting of chains, bands, hoops, earring posts, ear wires, ear clips, pins, and hair clasps.

13. A piece of jewelry for use by a person on said person's clothing or body, comprising:
   (a) a flat piece of porous material including a top surface and bottom surface opposite said top surface wherein both said top and bottom surfaces are operative to receive a fragrance producing composition that includes a fragrance emitting substance in a carrier liquid;
   (b) a securement member adapted to releasably secure to a portion of the person's body or clothing; and
   (c) a plurality of stanchions secured to said securement member, said stanchions operative to support said flat piece of porous material in spaced relation to said securement member.

14. A piece of jewelry according to claim 13 including a plurality of prongs formed as extensions of said stanchions, said prongs having upper end portions that curve inwardly toward one another thereby to retain said piece of porous material therein.

15. A piece of jewelry according to claim 13 wherein said piece of porous material has a shape selected from a group consisting of circles, ovals and n-sided polygons wherein n is an integer that is greater than 2.

16. A piece of jewelry according to claim 13 wherein said piece of porous material is a ceramic.

17. A piece of jewelry according to claim 16 wherein said ceramic contains sintered aluminum oxide.

18. A piece of jewelry according to claim 17 wherein said aluminum oxide has a particle size of between 4–7 micrometers, inclusively.

19. A piece of jewelry according to claim 13 wherein said securement member is selected from a group consisting of chains, bands, hoops, earring posts, ear wires, ear clips, pins, and hair clasps.

20. A piece of jewelry adapted to receive a quantity of a fragrance producing composition that includes a fragrance emitting substance in a carrier liquid comprising:
   (a) a securement member adapted to releasably secure to a portion of one's body or one's clothing;
   (b) a setting supported by said securement member, including
      (1) a plurality of stanchions secured thereto; and
      (2) prongs, formed as extensions of said stanchions, wherein each said prong has an upper end portion that is curved inwardly toward one another; and
   (c) a piece of porous material supported by said setting and retained therein by said prongs at an orientation relative to said securement member such that ambient air can flow between said piece and said securement member, said piece of porous material having sufficient porosity to permit penetration thereof by the carrier liquid and the fragrance emitting substance.

21. A piece of jewelry adapted to receive a quantity of a fragrance producing composition that includes a fragrance emitting substance in a carrier liquid comprising:
   (a) a securement member adapted to releasably secure to a portion of one's body or one's clothing;
   (b) a setting supported by said securement member; and
   (c) a piece of ceramic containing sintered aluminum oxide having a particle size of between 4–7 micrometers, inclusively and having sufficient porosity to permit penetration thereof by the carrier liquid and the fragrance emitting substance and further including a top surface and a bottom surface opposite said top surface, said piece affixed to said setting at an orientation relative to said securement member such that ambient air can flow about at least a portion of both the top and bottom surfaces.

22. A piece of jewelry adapted to receive a quantity of a fragrance producing composition that includes a fragrance emitting substance in a carrier liquid comprising:
   (a) a securement member adapted to releasably secure to a portion of one's body or one's clothing;
   (b) a setting supported by said securement member, said setting including a base and a plurality of stanchions secured thereto; and
   (c) a piece of porous material having sufficient porosity to permit penetration thereof by the carrier liquid and the fragrance emitting substance and including a top surface and a bottom surface opposite said top surface, said piece affixed to said setting in spaced-apart relation to said base and at an orientation relative to said securement member such that ambient air can flow between said base and said piece whereby air can flow about at least a portion of both the top and bottom surfaces.

23. A piece of jewelry according to claim 22 wherein prongs are formed as extensions of said stanchions, said prongs having an upper end portions that are curved inwardly toward one another thereby to retain said piece of porous material in said setting when said piece of porous material is supported thereby.

24. A piece of jewelry adapted to receive a quantity of a fragrance producing composition that includes a fragrance emitting substance in a carrier liquid comprising:
   (a) a securement member adapted to releasably secure to a portion of one's body or one's clothing;
   (b) a bezel supported by said securement member; and
   (c) a piece of porous material having sufficient porosity to permit penetration thereof by the carrier liquid and the fragrance emitting substance and including a top surface and a bottom surface opposite said top surface, said piece affixed to said setting in spaced-apart relation to said base and at an orientation relative to said securement member such that ambient air can flow between said base and said piece whereby air can flow about at least a portion of both the top and bottom surfaces.

25. A piece of jewelry adapted to receive a quantity of a fragrance producing composition that includes a fragrance emitting substance in a carrier liquid comprising:
   (a) a securement member adapted to releasably secure to a portion of one's body or one's clothing;
   (b) a setting supported by said securement member, said setting including a base; and
   (c) a piece of porous material having sufficient porosity to permit penetration thereof by the carrier liquid and the fragrance emitting substance and including a top surface and a bottom surface opposite said top surface, said piece affixed to said setting in spaced-apart relation to said base and at an orientation relative to said securement member such that ambient air can flow between said base and said piece whereby air can flow about at least a portion of both the top and bottom surfaces, wherein said piece of porous material includes a ribbed design thereon, said design protrudes from said piece of porous material so as to vary the thickness thereof.

26. A method of extending the scent of a selected fragrance on a piece of jewelry comprising the steps of:

(a) applying a quantity of a fragrance producing composition having a carrier liquid to a piece of ceramic containing sintered aluminum oxide that forms a component of the piece of jewelry, wherein said aluminum oxide has a particle size of between 4–7 micrometers, inclusively;

(b) exposing said piece of porous material to the ambient for a selected interval of time;

(c) after said interval of time, removing the scent of the fragrance by washing said piece of porous material in alcohol thereby to diffuse the carrier liquid; and repeating steps (a) and (b).

* * * * *